US008434641B2

(12) United States Patent
Coughlin et al.

(10) Patent No.: US 8,434,641 B2
(45) Date of Patent: May 7, 2013

(54) MEDICAMENT DISPENSING SYSTEM

(75) Inventors: Michael E. Coughlin, Mission Hills, KS (US); Shane P. Coughlin, Kansas City, MO (US); Timothy A. Giebler, Olathe, KS (US); Lawrence Guerra, Mission, KS (US)

(73) Assignee: ScriptPro LLC, Mission, KS (US)

( * ) Notice: Subject to any disclaimer, the term of this patent is extended or adjusted under 35 U.S.C. 154(b) by 1221 days.

(21) Appl. No.: 12/196,079

(22) Filed: Aug. 21, 2008

(65) Prior Publication Data

US 2009/0188935 A1 Jul. 30, 2009

Related U.S. Application Data

(60) Provisional application No. 61/023,311, filed on Jan. 24, 2008, provisional application No. 61/023,688, filed on Jan. 25, 2008.

(51) Int. Cl.
*G07F 11/16* (2006.01)
(52) U.S. Cl.
USPC ............................................ 221/174; 221/69
(58) Field of Classification Search .................. 221/1, 7, 221/64, 89, 90, 123, 124, 130, 131, 186, 221/188, 209, 241
See application file for complete search history.

(56) References Cited

U.S. PATENT DOCUMENTS

| 5,337,919 A | 8/1994 | Spaulding et al. |
| 5,713,487 A | 2/1998 | Coughlin |
| 5,762,235 A | 6/1998 | Coughlin |
| 5,798,020 A | 8/1998 | Coughlin et al. |
| 5,860,563 A | 1/1999 | Guerra et al. |
| 5,873,488 A | 2/1999 | Guerra |
| 5,897,024 A | 4/1999 | Coughlin et al. |
| 6,085,938 A | 7/2000 | Coughlin |
| 6,155,485 A | 12/2000 | Coughlin et al. |
| 6,161,721 A | 12/2000 | Kudera et al. |
| 6,318,630 B1 | 11/2001 | Coughlin et al. |
| 6,343,711 B1 | 2/2002 | Coughlin |
| 6,421,584 B1 | 7/2002 | Norberg et al. |
| 6,574,580 B2 | 6/2003 | Hamilton |
| 6,578,734 B1 | 6/2003 | Coughlin et al. |
| 6,592,005 B1 | 7/2003 | Coughlin et al. |
| 6,595,384 B2 * | 7/2003 | Takahashi ......................... 221/7 |
| 6,738,723 B2 | 5/2004 | Hamilton |
| 6,883,681 B1 | 4/2005 | Coughlin et al. |
| 6,905,046 B2 | 6/2005 | Coughlin et al. |
| 6,910,601 B2 | 6/2005 | Thomas et al. |
| 6,974,049 B2 * | 12/2005 | Williams et al. .............. 221/120 |
| 7,048,183 B2 | 5/2006 | Coughlin et al. |

(Continued)

*Primary Examiner* — Gene Crawford
*Assistant Examiner* — Kelvin L Randall, Jr.
(74) *Attorney, Agent, or Firm* — Hovey Williams LLP

(57) ABSTRACT

A system for storing a plurality of solid objects and dispensing the solid objects into a plurality of containers. The system comprises non-automated dispensing cells, physically actuated to dispense solid objects one at a time into one of the containers, and automated dispensing cells, electrically actuated to dispense solid objects from a holding tank simultaneously in bulk into one of the containers. The automated dispensing cells may independently dispense objects into the holding tank one at a time while a manipulator arm of the system simultaneously brings a container to one of the non-automated or automated dispensing cells. Then, when the manipulator arm brings a container to one of the automated dispensing cells, the solid objects may be dispensed into the container in bulk by simply opening a gate mechanism.

6 Claims, 8 Drawing Sheets

U.S. PATENT DOCUMENTS

| | | |
|---|---|---|
| 7,100,796 B1 | 9/2006 | Orr et al. |
| 7,121,427 B2 | 10/2006 | Guerra |
| 7,175,381 B2 | 2/2007 | Guerra |
| 7,230,519 B2 | 6/2007 | Coughlin et al. |
| 7,258,521 B2 | 8/2007 | Guerra et al. |
| 7,308,338 B2 | 12/2007 | Guerra |
| 2006/0180601 A1 | 8/2006 | Guerra |
| 2007/0057800 A1 | 3/2007 | Coughlin et al. |

* cited by examiner

MEDICAMENT DISPENSING SYSTEM

RELATED APPLICATIONS

This nonprovisional patent application claims priority benefit, with regard to all common subject matter, of earlier-filed U.S. provisional patent applications titled "Medicament Dispensing System", Ser. No. 61/023,311, filed Jan. 24, 2008 and Ser. No. 61/023,688, filed Jan. 25, 2008. The identified earlier-filed applications are hereby incorporated by reference in their entirety into the present application.

BACKGROUND

1. Field

The present technology relates to medicament dispensing systems. More particularly, embodiments of the technology involve a medicament dispensing system operable to pre-load medicaments at individual robotic cell multiplexor (RCM) stations and dispense the medicaments into vials of varying sizes.

2. Related Art

Pharmacists spend an increasing amount of time educating patients about proper use and handling of medicaments and pharmaceuticals. While this trend toward more patient counseling increases patients' knowledge about medicaments and decreases improper use of medicaments, it leaves less time for pharmacists to fill and dispense medicaments.

Automated medicament dispensing systems have been developed to automate some medicament filling and dispensing steps to allow pharmacists to spend more time with patients. For example, U.S. Pat. No. 5,337,919 discloses an automatic medicament dispensing machine having a plurality of dispensing cells for storing and dispensing various types of solid medicament units such as pills, capsules and caplets. Each cell includes a rotatable platen presenting a driven gear. A manipulator arm of the machine retrieves an empty vial and positions the vial adjacent the outlet of a selected dispensing cell. The manipulator arm includes a drive gear that engages the driven gear of the cell for selective rotation thereof in order to dispense medicament from the cell. The filled vial is then positioned on a discharge conveyor for subsequent handling such as labeling.

Similarly, U.S. Pat. No. 5,897,024 discloses a medicament dispensing cell for singulating various types of solid medicament to be dispensed one at a time. In this way, a counting device attached to either the medicament dispensing cell or the manipulator arm below the outlet of a selected dispensing cell may count the number of solid medicament units that have been dispensed into the vial and may stop dispensing once the desired count is reached.

However, the medicament dispensing cells disclosed above have the disadvantage of requiring that the manipulator arm hold the vial under one of the medicament dispensing cells until each pill has been counted and dispensed into the vial. Therefore the speed at which multiple prescriptions can be filled is greatly limited by the speed at which individual medicament units can be dispensed by a medicament dispensing cell.

Accordingly, there is a need for an improved system and apparatus for dispensing medicament units that does not suffer from the problems and limitations of the prior art.

SUMMARY

The present invention provides an improved system and apparatus for dispensing medicament units. Particularly, embodiments of the present technology provide a system and apparatus for storing a plurality of solid objects and dispensing the solid objects into a plurality of containers or vials. The system may be a medicament dispensing system operable to pre-load solid objects such as medicaments at individual robotic cell multiplexor (RCM) stations or dispensing cells, and to dispense the solid objects into vials of varying sizes.

The system may comprise a control system and a cabinet containing both non-automated dispensing cells and automated dispensing cells, as well as a manipulator arm for taking vials to and from the dispensing cells. The control system may comprise a processor for receiving prescriptions or scripts and providing corresponding control signals to various actuators within the system. The non-automated dispensing cells may be physically actuated by the manipulator arm to dispense solid objects one at a time into one of the vials. The automated dispensing cells may be electrically actuated to dispense solid objects from a holding tank, in bulk, into one of the vials.

Each of the automated dispensing cells may include a first storage bin and a holding tank. The first storage bin may store the solid objects and dispense the solid objects one at a time into the holding tank. The holding tank may comprise adjustable sidewalls for expanding and contracting the cross-sectional area and therefore the volume of the holding tank. The automated dispensing cells may further comprise a gate mechanism having a first position for retaining the solid objects in the holding tank and a second position for allowing the contents of the holding tank to empty into one of the vials.

The holding tank may further comprise at least one spring for biasing a portion of the sidewalls at a maximum expansion position. At the maximum expansion position, the holding tank may hold a maximum amount of the plurality of solid objects. Furthermore, a first actuator of each of the automatic dispensing cells may apply a force to the sidewalls opposing the force of the at least one spring to decrease the cross-sectional area of the holding tank. Therefore, the sidewalls of the holding tank may be adjusted to correspond with size of the vial required for a given prescription entered into the control system.

The automatic dispensing cell may also comprise a solid object counter disposed between an outlet of the first storage bin and the holding tank for sensing when a desired number of solid objects have passed into the holding tank. Furthermore, the automatic dispensing cell may comprise a second actuator for pivoting the holding tank and the gate mechanism away from the first storage bin to a position for dropping the solid objects from the holding tank into one of the vials.

The automated dispensing cells may operate in parallel to other operations of the system. For example, the first storage bin of the automated dispensing cells may independently count and dispense objects into the holding tank, one at a time, while the manipulator arm simultaneously brings one of the vials to one of the non-automated or automated dispensing cells. Then, when the manipulator arm brings one of the vials to one of the automated dispensing cells, the solid objects may be dispensed into the container, all at once, in bulk, by simply opening a gate mechanism. These and other important aspects of the present invention are described more fully in the detailed description below.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

Preferred embodiments of the present invention are described in detail below with reference to the attached drawing figures, wherein.

Figure 1:
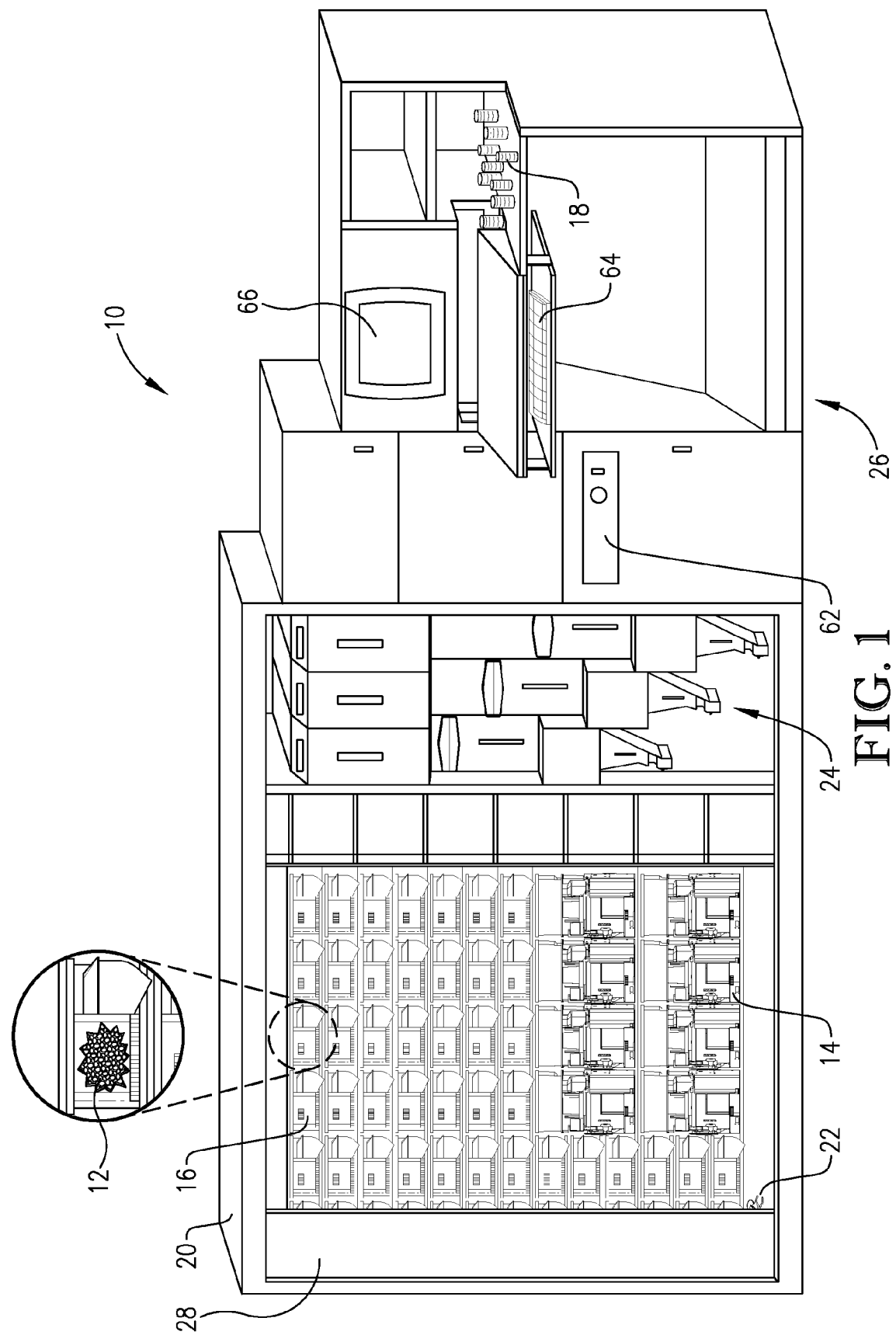
FIG. 1 is a schematic view of an automatic medicament dispensing system having a plurality of automated and non-automated dispensing cells in accordance with an embodiment of the present invention.

The drawing figures do not limit the present invention to the specific embodiments disclosed and described herein. The drawings are not necessarily to scale, emphasis instead being placed upon clearly illustrating the principles of the invention.

DETAILED DESCRIPTION

The following detailed description of embodiments of the invention references the accompanying drawings that illustrated specific embodiments in which the technology can be practiced. The embodiments are intended to describe aspects of the invention in sufficient detail to enable those skilled in the art to practice the invention. Other embodiments can be utilized and changes can be made without departing from the scope of the claims. The following detailed description is, therefore, not to be taken in a limiting sense. The scope of the present invention is defined only by the appended claims, along with the full scope of equivalents to which such claims are entitled.

Embodiments of the present invention, as illustrated in FIG. 1, provide a medicament dispensing system 10 operable to pre-load solid objects 12, such as medicaments, at individual robotic cell multiplexor (RCM) stations or dispensing cells 14,16, and to dispense the pre-loaded solid objects 12 into vials 18 of varying sizes. The system 10 may comprise a cabinet 20 containing a plurality of automated dispensing cells 14, a plurality of non-automated dispensing cells 16, and a manipulator arm 22 for carrying vials 18 to and from the dispensing cells 14,16.

The system may further comprise at least one medicine vial dispensing apparatus 24 for storing and dispensing empty vials 18 and a control system 26 for providing instructions to the manipulator arm 22 and the automated medicament dispensing cells 14. Various components of the system 10 may be operationally similar to the type illustrated in U.S. Pat. No. 5,337,919, hereby incorporated by reference in its entirety as part of this disclosure to an extent not inconsistent with this disclosure.

An exemplary cabinet 20 of the system 10 may comprise four automated cells 14, eight automated cells 14, fourteen automated cells 14, or any number of automated cells 14 desired for a given application. Additionally, the cabinet 20 may comprise any number of non-automated cells 16 as desired for a given application. The dispensing cells 14,16 may generally be arranged in rows and columns within the cabinet 20, though any physical arrangement of the dispensing cells 14,16 may be used. In various embodiments of the invention, the automated cells 14 are primarily located in a bottom portion of the cabinet 20.

The cabinet 20 may further comprise a sliding track 28 which may slide horizontally along the width of the cabinet 20, carrying the manipulator arm 22 back and forth across the cabinet 20. Additionally, the manipulator arm 22 may slide vertically up and down the length of the cabinet 20 along the sliding track 28.

Figure 2:
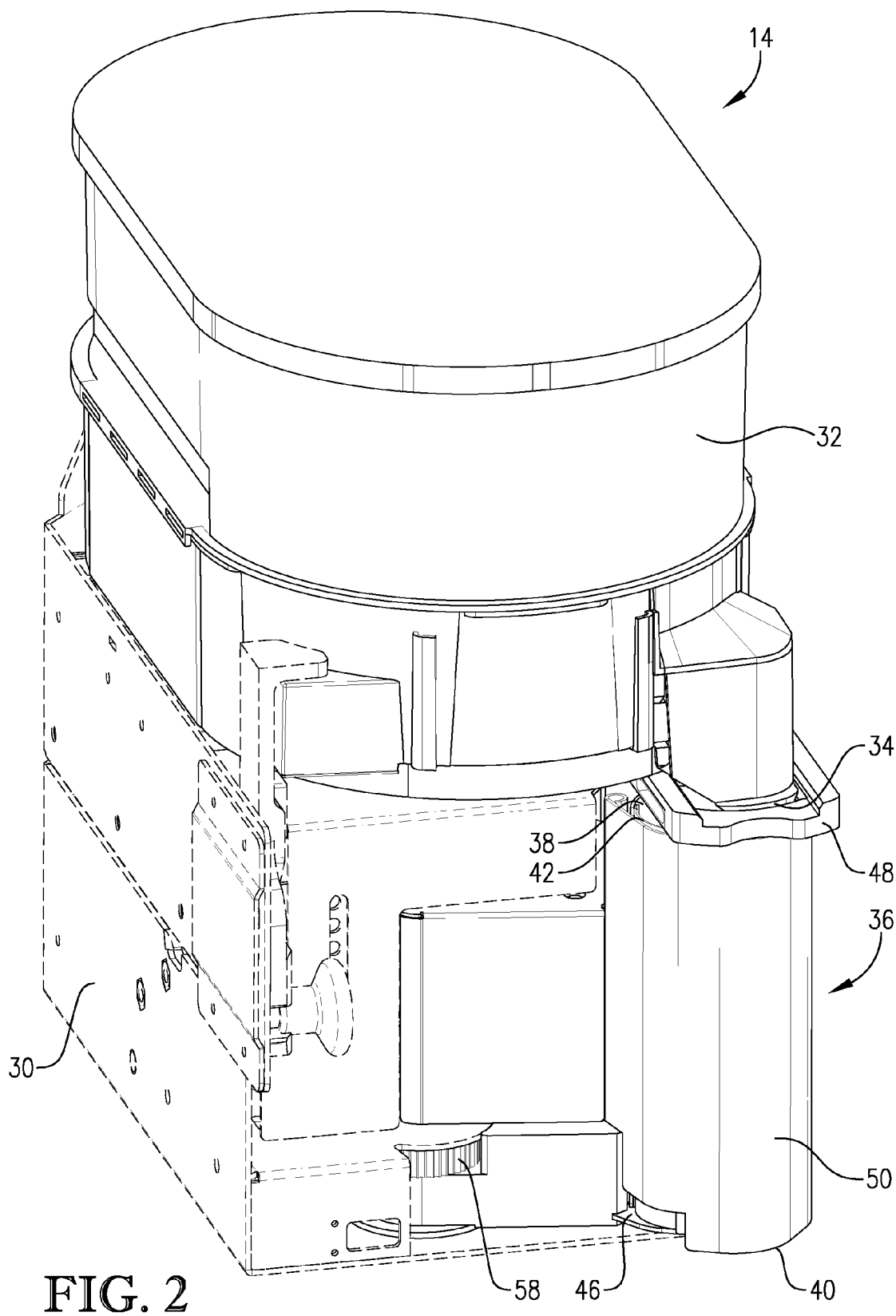
FIG. 2 is an isometric view of one of the automated dispensing cells of FIG. 1.
Figure 3:
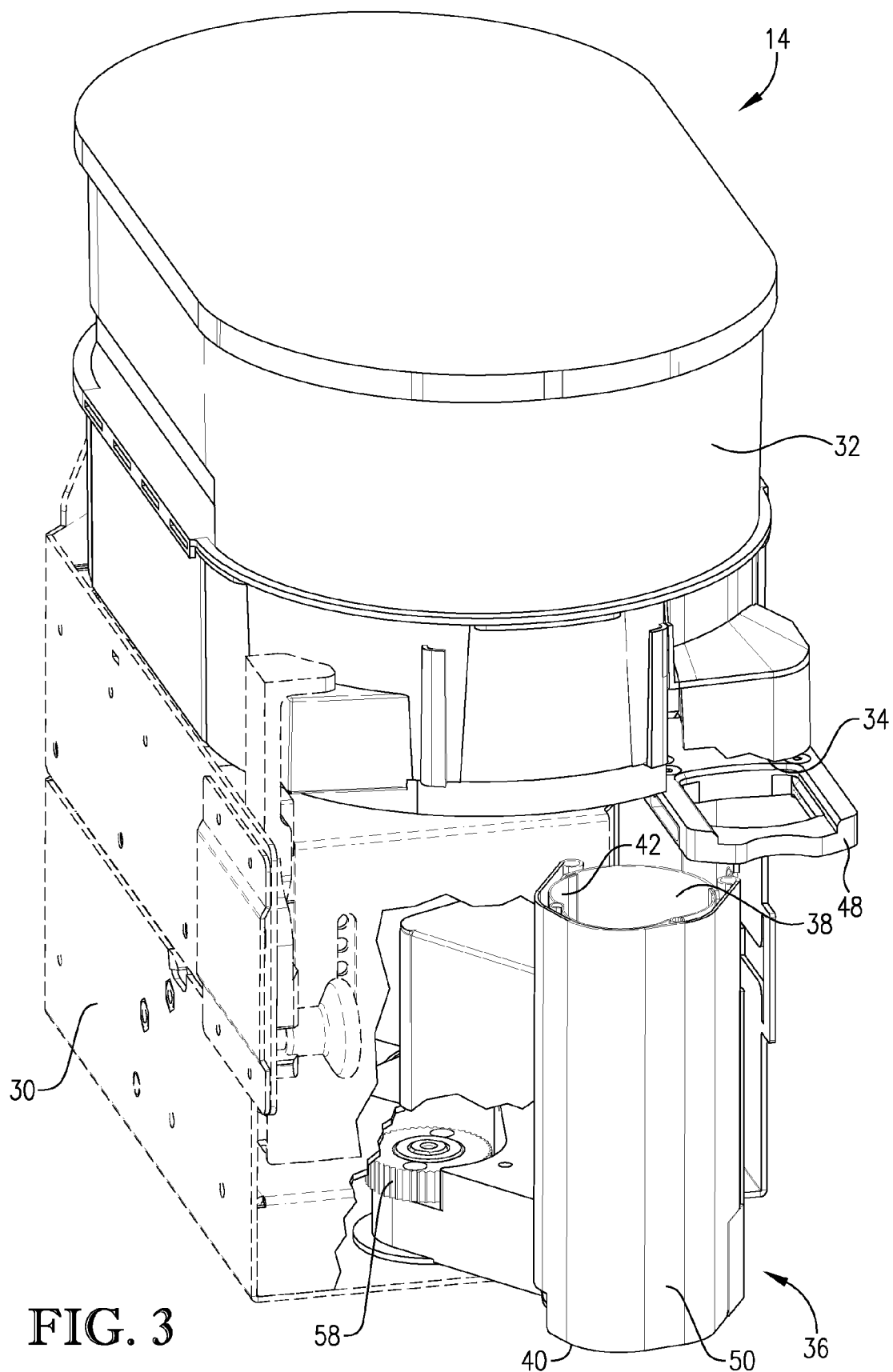
FIG. 3 is an isometric view of one of the automated dispensing cells of FIG. 1 with a holding tank pivoted away from a housing of the automated dispensing cell.

As illustrated in FIG. 2, each of the automated medicament dispensing cells 14 may comprise a housing 30, a first storage bin 32; a holding tank 36; a first actuator 44 (as depicted in FIGS. 4-7); and a gate mechanism 46. The holding tank 36 may rest adjacent the housing 30 in a first position, as illustrated in FIG. 2, or may pivot outward to a second position at a short distance away from the housing 30, as illustrated in FIG. 3.

The first storage bin 32 of the automated dispensing cells 14 may have an outlet 34 and may contain the plurality of solid objects 12. The first storage bin 32 may be similar in operation to the medicament dispensing cells described in U.S. Pat. No. 5,897,024 (the '024 patent), hereby incorporated by reference in its entirety as part of this disclosure to an extent not inconsistent with this disclosure. Therefore, the first storage bin 32 may comprise a housing defining a storage section or reservoir for storing the solid objects 12, a discharge section, a rotatable platen presenting a driven gear, and a dispensing assembly for dispensing solid objects 12 in single file, one at a time, from the storage section to the discharge section, as described and illustrated in the '024 patent. The outlet 34 may be located at a bottom portion of the discharge section.

The driven gear of the rotatable platen of the first storage bin 32 may be driven internally by a self-contained drive gear (not shown) which is operable to rotate the platen without requiring external physical manipulation. The self-contained drive gear may be at least communicably coupled with and receive actuation signals from the control system 26. The first storage bin 32 may further comprise a solid object counter 48 disposed between the outlet 34 of the first storage bin 32 and the holding tank 36 for sensing when a desired number of solid objects 12 have passed through the outlet 34 and into the holding tank 36.

The holding tank 36 may have a top opening 38, a bottom opening 40, and adjustable sidewalls 42. The sidewalls 42 may comprise one continuous sidewall or a plurality of sidewalls forming a substantially continuous sidewall 42. Additionally, the sidewalls may have two side edges 56 which may either touch one another or have a gap therebetween, as described below. The top opening 38 may have substantially the same shape, size, and cross-sectional area as the bottom opening 40. Additionally, the holding tank may have an outer casing 50 surrounding at least a portion of the sidewalls 42.

In various configurations, the holding tank 36 may be substantially tubular, having annular adjustable sidewalls. However, the holding tank 36 may be of any shape having a substantially uniform cross-sectional area at all points throughout its length. For example, the cross sectional area at the top opening 38 of the holding tank 36 may be substantially equal to the cross sectional area at the bottom opening 40, with the cross sectional area at all points between the top opening 38 and the bottom opening 40 being substantially equal. Having a uniform cross-sectional area throughout the length of the holding tank 36 is advantageous because it reduces the likelihood of the solid objects 12 bottlenecking inside of the holding tank 36 when the gate mechanism 46 is opened, as discussed below. Alternatively, the cross-sectional area may increase from the top opening 38 to the bottom opening 40.

Figure 4:
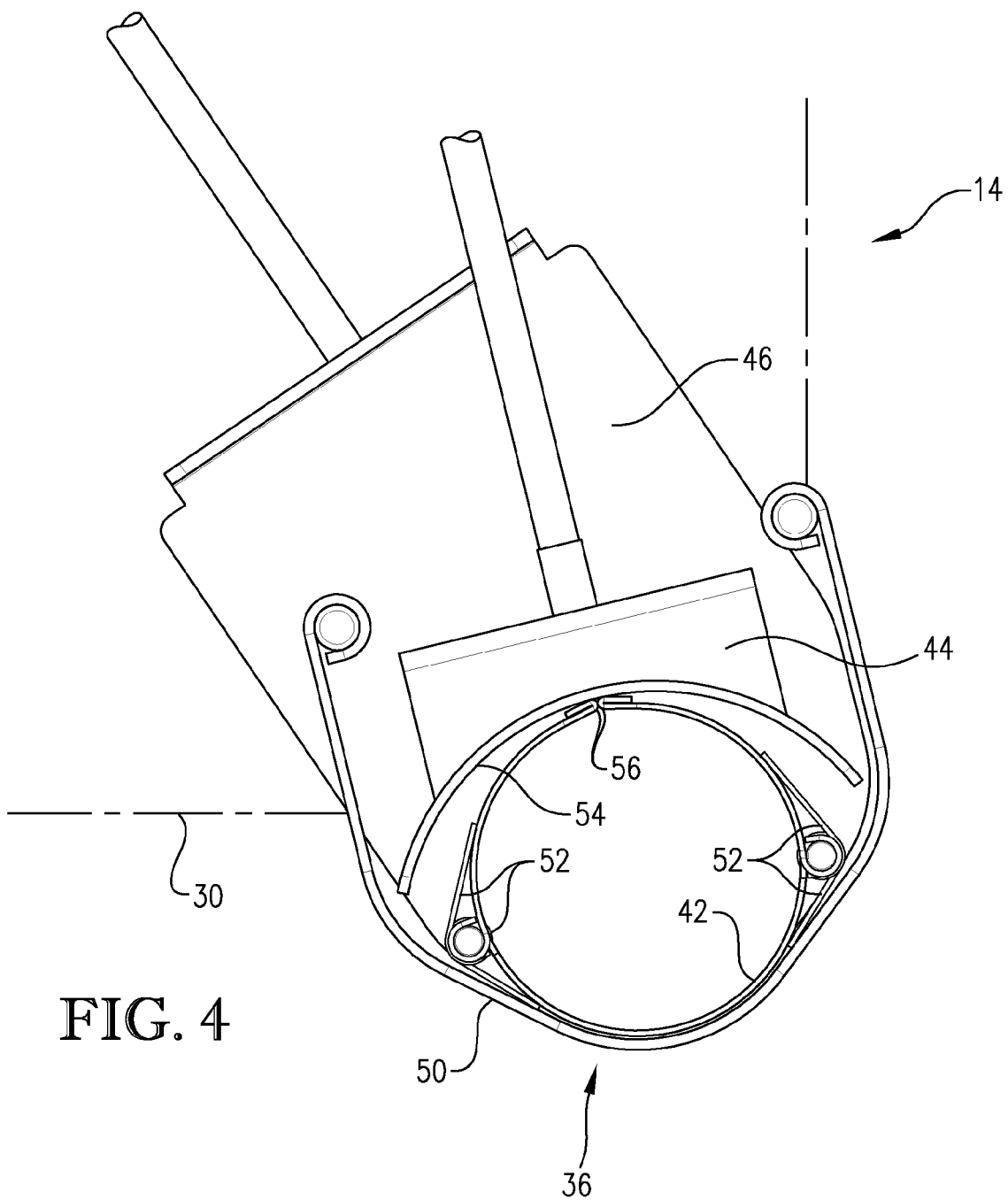
FIG. 4 is a top plan view of the holding tank of the automated dispensing cell and a first actuator at a maximum contraction position.
Figure 5:
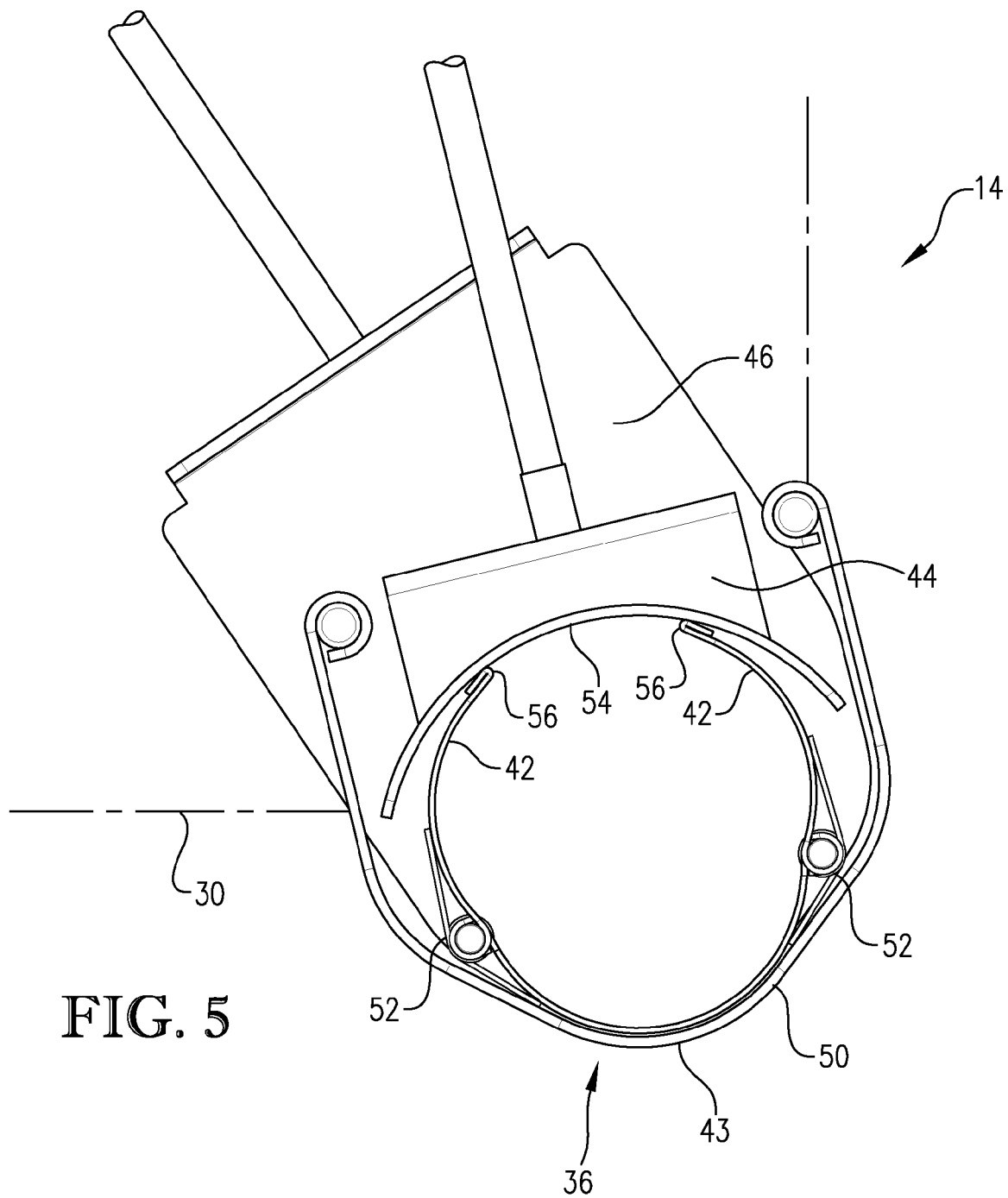
FIG. 5 is a top plan view of the holding tank of the automated dispensing cell and the first actuator at an intermediate contraction position.

The adjustable sidewalls 42 may allow for the holding tank 36 to have an adjustable volume for temporarily holding a desired amount of the solid objects 12, such as solid medicament objects like pills, capsules, and caplets. At least a portion of the sidewalls 42 of the holding tank 36 may be actuated to uniformly expand or contract the cross-sectional area inward of the sidewalls. Specifically, the holding tank 36 may have at least a maximum contraction position, as illustrated in FIG. 4, an intermediate contraction position, as illustrated in FIG. 5, and a maximum expansion position, as illustrated in FIG. 6.

Figure 6:
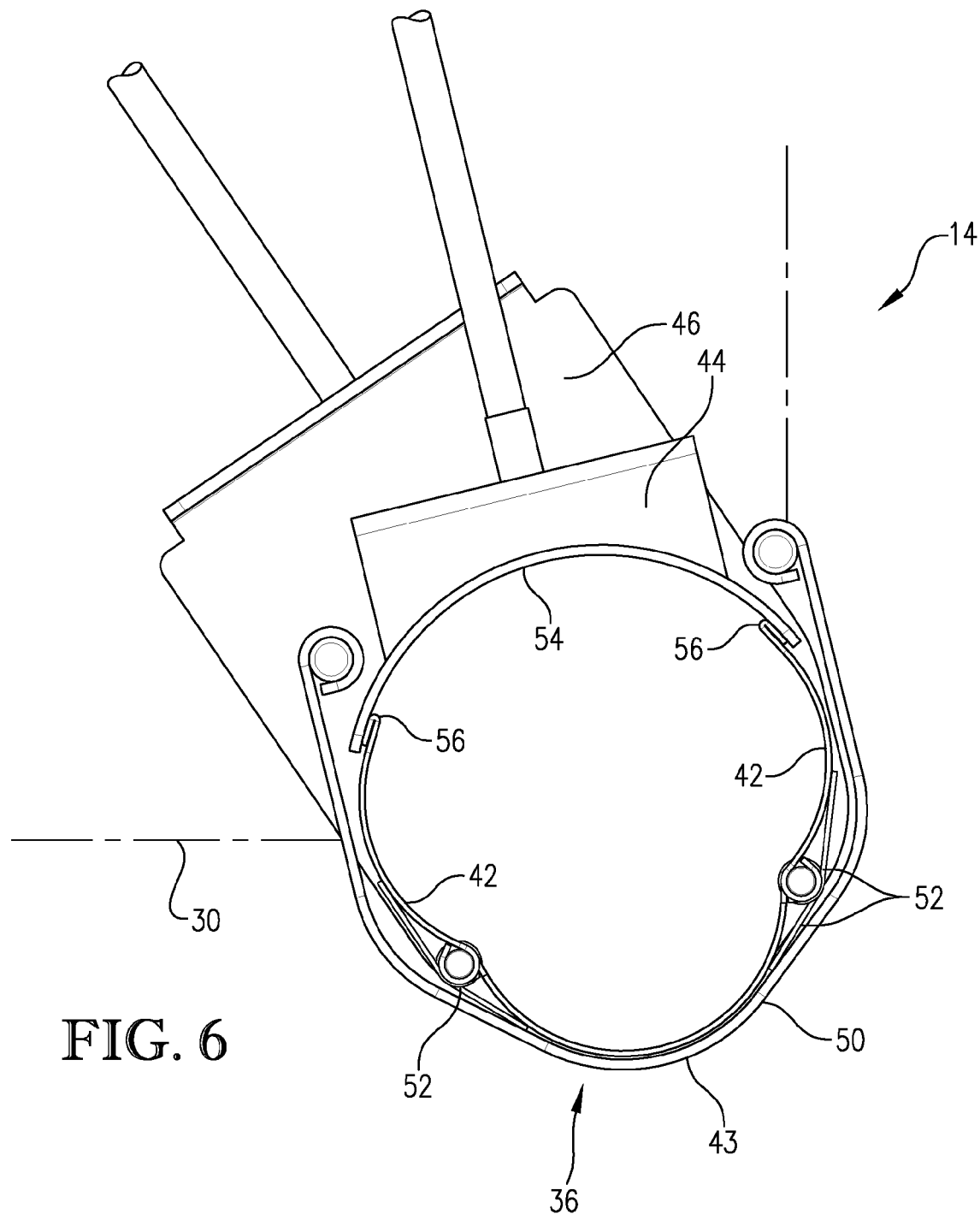
FIG. 6 is a top plan view of the holding tank of the automated dispensing cell and the first actuator at a maximum expansion position.

In various embodiments of the invention, portions of the sidewalls 42 may be attached to or integral with at least one spring 52 for biasing at least a portion of the sidewalls 42 at the maximum expansion position illustrated in FIG. 6. At the maximum contraction position, the holding tank 36 may hold a minimum amount of the solid objects 12, and at the maximum expansion position, the holding tank 36 may hold a maximum amount of the solid objects 12. The intermediate contraction position may be a fixed position or may refer to any position between the maximum contraction position and the maximum expansion position.

The first actuator 44 may be used to actuate at least a portion of the sidewalls 42 of the holding tank 36, adjusting the sidewalls 42 to various positions. For example, the first actuator 44 may be a force-applying actuator which decreases the cross-sectional area inward of the sidewalls 42 by pushing against portions of the sidewalls 42. The first actuator 44 may comprise a containment portion 54 which makes contact with a portion of the sidewalls 42 for actuating the sidewalls 42, and which may block the gap between the two side edges 56 of the sidewalls 42. The containment portion 54 may extend the full length of the holding tank 36 and may bridge a gap between the two side edges 56 of the sidewalls 42. The containment portion 54 provides containment when the sidewalls 42 alone do not form a 360-degree boundary. For example, at the maximum expansion position, as illustrated in FIG. 6, the containment portion 54 of the first actuator 44 may supplement the sidewalls 42. However, in the maximum contraction position illustrated in FIG. 4, the sidewalls 42 may form a 360-degree boundary, with the side edges 56 touching. In this position, the containment portion 54 merely holds the two side edges 56 together by applied force. Additionally, the first actuator 44 may have a set number of positions which each provide the holding tank 36 with a cross-sectional area corresponding to the cross-sectional area of one of the available vials 18. For example, in one embodiment of the invention, three different vial sizes are available. Therefore, if a prescription sent to the control system 26 requires a particularly-sized vial, the first actuator 44 may be provided with a signal to for adjusting the sidewalls 42 of the holding tank 36 to the appropriate position such that the cross-sectional area of the holding tank 36 is substantially equal to or less than the cross-sectional area of the vial.

Figure 7:
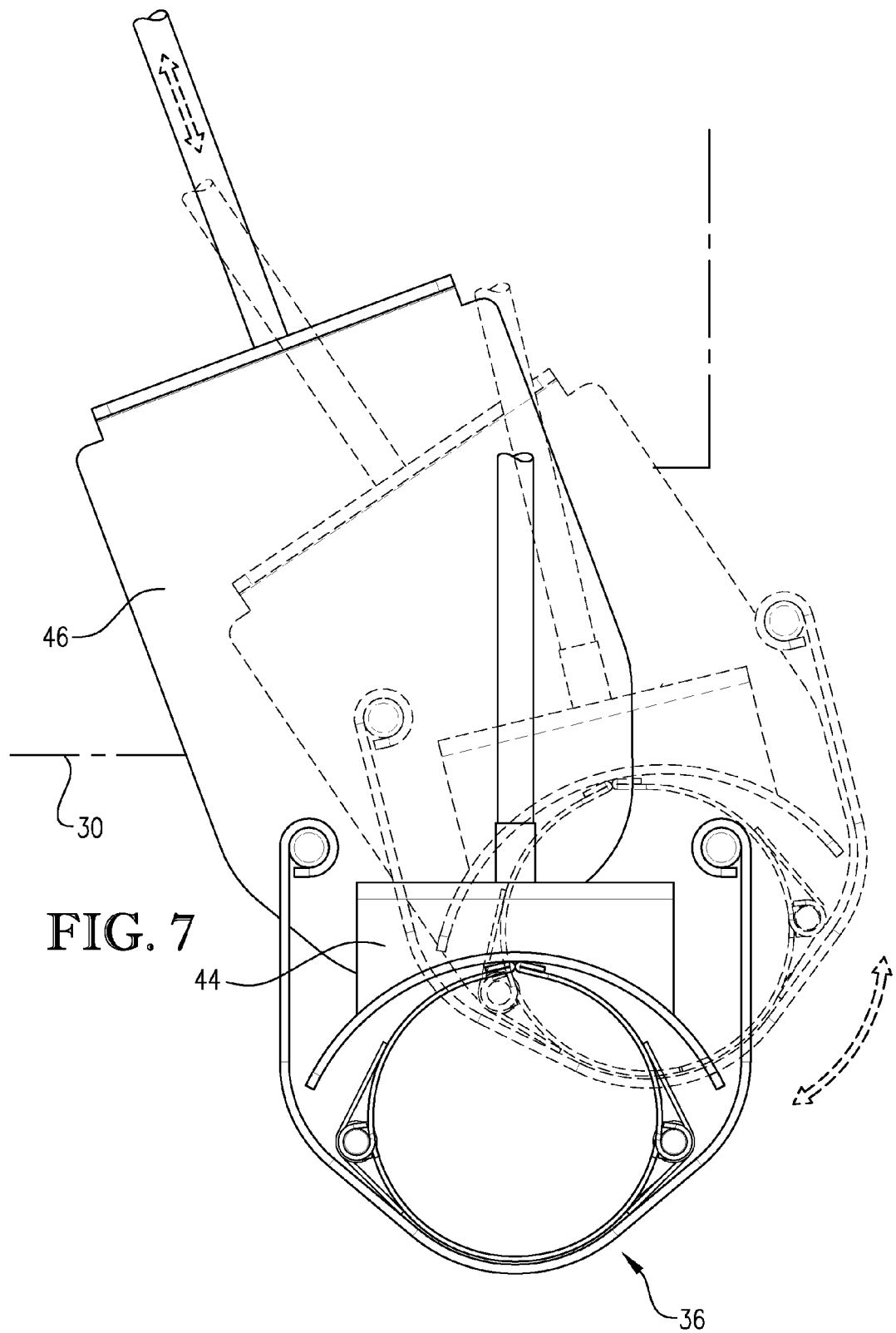
FIG. 7 is a top plan view of the holding tank of the automated dispensing cell and a gate mechanism, wherein FIG. 7 illustrating the holding tank's motion from its position in FIG. 2 to its position in FIG. 3, as well as the motion of the gate mechanism opening.

The gate mechanism 46 may be of any shape, sized to completely block the bottom opening 40. The gate mechanism 46 may have a first position, as shown in FIGS. 4-6, for blocking the bottom opening 40 of the holding tank 36 to retain the solid objects 12 in the holding tank 36, and a second position, as shown in FIG. 7, for allowing the solid objects 12 of the holding tank 36 to drop into one of the empty vials 18. The first storage bin 32 may preferably dispense at least a portion of the solid objects 12 through the outlet 34 into the holding tank 36 only when the gate mechanism 46 is in the first position.

FIG. 7 illustrates a range of motions that may be performed by the gate mechanism 46 and the holding tank 36. The gate mechanism 46 may transition from the first position to the second position by sliding laterally out of the way of the bottom opening 40 by way of some type of actuator. Alternatively, the gate mechanism 46 may be pivoted downward on a hinge or be moved away from the bottom opening 40 in any manner known in the art.

As earlier described, the holding tank 36 may rest adjacent the housing 30 in a first position, as illustrated in FIG. 2, or may pivot outward to a second position at a short distance away from the housing 30, as illustrated in FIG. 3. Therefore, the automated cell 14 may further comprise a second actuator 58 for pivoting the holding tank 36 and the gate mechanism 46 away from the first storage bin 32 to a position for dropping the solid objects 12 from the holding tank 36 into one of the empty vials 18. So, as illustrated in FIG. 7, the gate mechanism 46 and the holding tank 36 may pivot outward together, prior to moving the gate mechanism 46 away from the bottom opening 40 of the holding tank 36.

The non-automated medicament dispensing cells 16 may be similar in operation to the medicament dispensing cells described in U.S. Pat. No. 5,897,024, as earlier incorporated by reference in its entirety as part of this disclosure to an extent not inconsistent with this disclosure. The non-automated dispensing cells 16 may comprise a housing defining a storage section, a discharge section, a rotatable platen presenting a driven gear, and a dispensing assembly for dispensing solid objects 12 in single file from the storage section to the discharge section, as described and illustrated in the '024 patent. From the discharge section, the solid objects 12 may fall out through the outlet 34 into one of the empty vials 18. The driven gear of the rotatable platen of each of the non-automated medicament dispensing cells 16 may be driven by a drive gear (not shown) of the manipulator arm 22.

The medicine vial dispensing apparatus 24 may be of the type described in U.S. Pat. No. 5,860,563, hereby incorporated by reference in its entirety as part of this disclosure to an extent not inconsistent with this disclosure. The medicine vial dispensing apparatus 24 may comprise multiple medicine vial dispensing apparatuses constructed to store and dispense vials of differing volumes or diameters. For example, small-diameter vials may have volumes of 12 drams, 13 drams, or 16 drams. Medium-diameter vials may have a volume of 20 drams. Large-diameter vials may have a volume of 30 drams or 40 drams. However, vials of any volume or diameter may be used.

Figure 8:
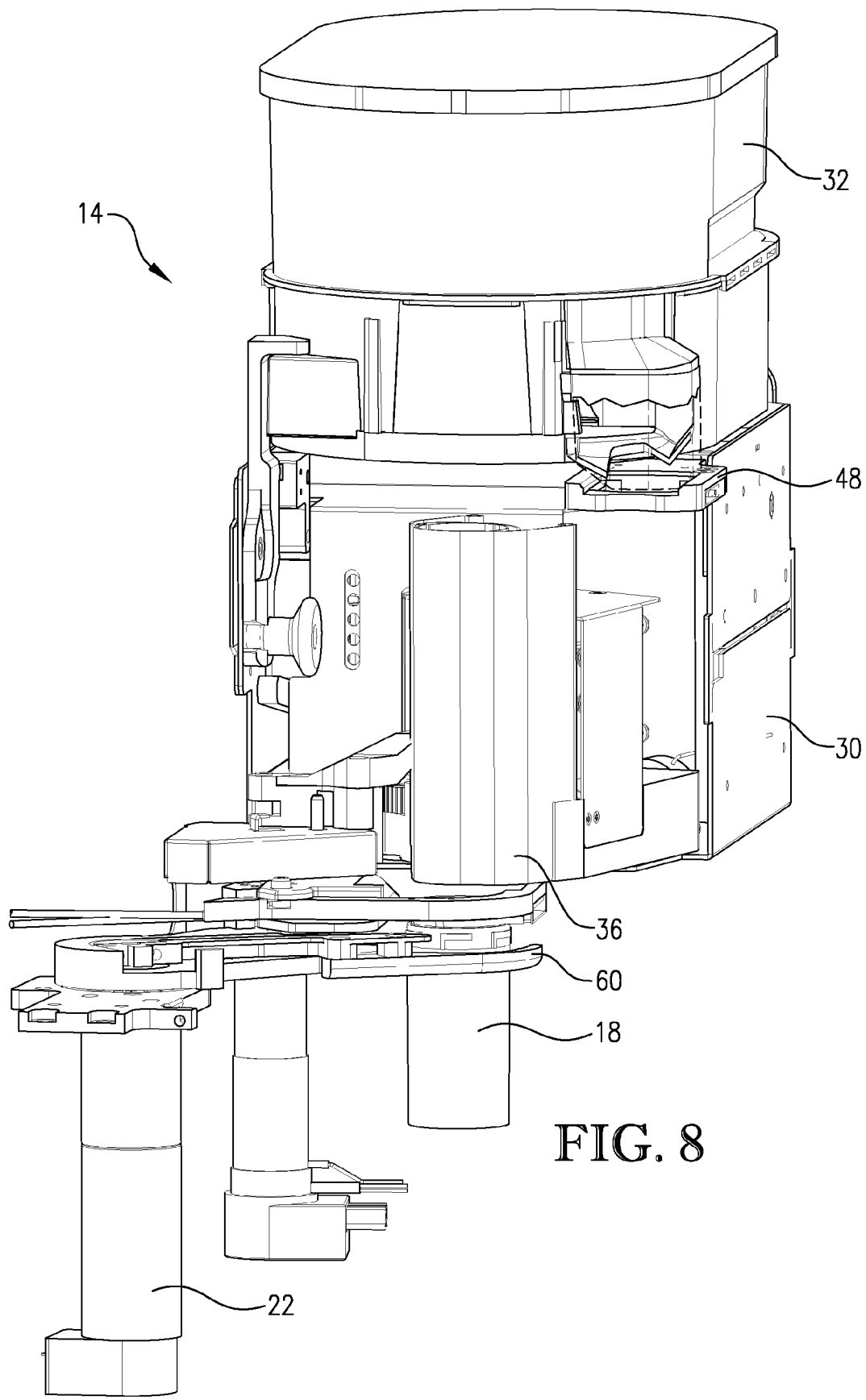
FIG. 8 is an isometric view of one of the automated dispensing cells, with the holding tank pivoted away from the housing and a manipulator arm holding a vial underneath the holding tank.

The manipulator arm 22, as illustrated in FIG. 8, may be a robotic arm for taking an empty vial to any of the dispensing cells 14,16 of the dispensing system 10. The manipulator arm 22 may comprise a vial gripper 60, such as the vial gripper described in U.S. Pat. No. 5,873,488, hereby incorporated by reference in its entirety as part of this disclosure to an extent not inconsistent with this disclosure. The manipulator arm 22 may further include a drive gear (not shown) for engaging the driven gear (not shown) of the non-automated dispensing cell 16 for selective rotation thereof in order to dispense the solid objects 12 from the non-automated dispensing cell 16 into one of the vials 18.

The control system 26 may comprise a processor 62 for receiving prescriptions (scripts) and providing corresponding control signals to various actuators within the system 10, a bar code scanner (not shown) or other indicia reader, an input device 64, a display 66, and a label printer (not shown).

The processor 62 may include any number of processors, controllers, integrated circuits, programmable logic devices, or other computing devices and resident or external memory for storing data and other information accessed and/or generated by the system 10. The processor 62 may be coupled with the display 66, the memory, the input device 64, the label printer, and other components through wired or wireless connections, such as a data bus (not shown), to enable information to be exchanged between the various components.

The processor 62 may implement a computer program and/or code segments to perform the functions described herein. The computer program preferably comprises an ordered listing of executable instructions for implementing logical functions in the processor 62. The computer program can be embodied in any computer-readable medium for use by or in connection with an instruction execution system, apparatus, or device, and execute the instructions. In the context of this application, a "computer-readable medium" can be any means that can contain, store, communicate, propagate, or transport the program for use by or in connection with the instruction execution system, apparatus, or device. The computer-readable medium can be, for example, but not limited to, an electronic, magnetic, optical, electromagnetic, infrared, or semi-conductor system, apparatus, device or propagation medium. More specific, although not inclusive, examples of the computer-readable medium would include the following: an electrical connection having one or more wires, a portable computer diskette, a random access memory (RAM), a read-only memory (ROM), an erasable, programmable, read-only memory (EPROM or Flash memory), an optical fiber, and a portable compact disk read-only memory (CDROM).

The memory may be integral with the system 10, integral with the processor 62, stand-alone memory, or a combination of both. The memory may include, for example, removable and non-removable memory elements such as RAM, ROM, flash, magnetic, optical, USB memory devices, and/or other conventional memory elements.

The memory may store various data associated with the operation of the system 10, such as the computer program and code segments mentioned above, or other data for instructing the processor 62 and system 10 elements to perform the steps described herein. Further, the memory may store data regarding the identification, location, and status of each cell 14,16 within the system 10 as well as information about the solid objects 12 contained in the cells 14,16. The various data stored within the memory may also be associated within one or more databases to facilitate retrieval of the information.

The input device 64 permits a user to operate the system 10 and enables users, third parties, or other devices to share information with the processor 62. The input device 64 may comprise one or more functionable inputs such as buttons, switches, scroll wheels, a touch screen associated with the display 66, voice recognition elements such as a microphone, pointing devices such as mice, touchpads, tracking balls, styluses, a camera such as a digital or film still or video camera, combinations thereof, etc. Further, the input device 64 may comprise wired or wireless data transfer elements such as a removable memory including the memory, data transceivers, etc., to enable the user and other devices or parties to remotely interface with the system 10. The device may also include a speaker for providing audible instructions and feedback.

The input device 64 may be operable to provide various information to the user utilizing the display 66 or other visual or audio elements such as a speaker. Thus, the input device 64 enables the user and system 10 to exchange information relating to the system 10, including content of the cells 14,18, configuration information, security information, preferences, manipulator arm 22 routing information, order and priority of various prescriptions, alerts and alert notification, etc. For example, a user may enter product identification numbers via the input device 64 and may enter in at least one prescription to be filled, as well as data to be printed on the label corresponding to the prescription.

The bar code scanner may be user-operated or may be integral with the manipulator arm 22 and may be any type of indicia reader known in the art. The bar code scanner may scan in information about the product and its expiration date, which may be found on a product container and/or a bar code placed on each of the dispensing cells 14,16. The solid objects 12 loaded into the cells 14,16 may be individually identified by a national drug code (NDC), drug identification number (DIN), unit of work (UOW) ID, or other identification numbers. The identification numbers are preferably bar coded on the products but may also be merely printed thereon.

The display 66 may be coupled with the processor 62 and is operable to display various information corresponding to the system 10 and its cells 12,16. For example, the display 66 may display user-entered information as well as data regarding what scripts have been filled, if any of the cells 14,16 are empty or near empty, if there is a system error, etc. The display 66 may comprise conventional black and white, monochrome, or color display elements including CRT, TFT, LCD, and/or plasma display devices. Additionally, the display 66 may be integrated with the input device 64, such as in embodiments where the display 66 is a touch-screen display to enable the user to interact with it by touching or pointing at display areas to provide information to the control system 26.

The label printer may be any printer known in the art and may receive data from the processor 62 corresponding to a particular prescription. In various embodiments of the invention, the label printer may be operable to print on various types, colors, and sizes of labels, depending on the commands received from the processor 62. The labels may be placed onto the vials 18 at any point before, during, or after processing of the prescription by a user, manually, or via an automated labeling device.

In use, the system 10 may receive at least one script or prescription entered by a user, such as a pharmacist, via the input device 64. The control system 26 may then command the manipulator arm 22 to grip one of the empty vials 18 of a desired volume. If the script requests solid objects 12 that are contained in one of the non-automated cells 16, then the manipulator arm 22 may place one of the empty vials 18 under the outlet 34 of the desired non-automated cell and the solid objects 12 may be dispensed, one solid object 12 at a time, into the vial.

If the script requests a selected quantity or volume of solid objects 12 that are contained in one of the automated cells 14, then that automated cell may activate the first actuator 44 to resize the volume and cross-sectional area of the holding tank 36 as required. Then the automated cell may begin dispensing the solid objects 12 into its holding tank 36 simultaneously while the manipulator arm 22 grips one of the empty vials 18 and moves the vial to a position under the holding tank 36. Once the proper quantity or volume of solid objects 12 have been dispensed into the holding tank 36, the holding tank 36 may pivot outward (along with the gate mechanism 46) to a position such that the bottom opening 40 is aligned with a top opening of the vial. Then, the gate mechanism 46 may be actuated to move away from the bottom opening 40, allowing the solid objects 12 to drop into the vial. Once filled, the vial may then be positioned on a discharge conveyor, counter top, etc. for subsequent handling such as labeling and manual inspection by a pharmacist.

In various embodiments of the invention, the first actuator 44 may actuate the holding tank 36 to flutter, quickly expanding and contracting, when the gate mechanism 46 is slid out from under the holding tank 36, such that any solid objects 12 stuck in the holding tank 36 may be knocked loose and fall into the vial. Alternatively, the holding tank 36 may be actuated to vibrate to insure that all contents are dropped into the vial.

The processor 62 may analyze the scripts to be filled and determine the most efficient order in which to process those scripts. Alternatively, the processor 62 may instruct the system 10 to fill the scripts in the order in which they are received. The processor 62 may also instruct one or more of the automated dispensing cells 14 to dispense a desired number of solid objects 12 into the holding tank 36 for a given prescription while instructing the manipulator arm 22 to simultaneously move to another one of the dispensing cells 14,16 to fill a different prescription.

Note that it may still be necessary for both the automated and non-automated dispensing cells 14,16 to singulate the solid objects 12 in order to count how many solid objects 12 are placed in the vials 18. However, by using the holding tank 36, this singulation may be performed independent of the manipulator arm 22, therefore allowing multiple cells 14,16 to perform singulation of solid objects simultaneously. Therefore, the proper number of solid objects 12 can be prepared prior to placement of one of the vials 18 under the holding tank 36, allowing the solid objects 12 to be dispensed in one swift motion. This increases the speed at which multiple scripts may be processed.

For example, three prescriptions may be entered via the input device 64 by a user, each for a different type of the solid objects 12. In this example, a quantity of twenty may be requested for each prescription, and two types of the requested solid objects may be contained in automated dispensing cells 14, while one type of the solid objects may be contained in one of the non-automated dispensing cells 16. The manipulating arm 22 may grip one of the vials 18 of a proper size and may first travel to the non-automated dispensing cell. The non-automated dispensing cell 16 may dispense twenty solid objects 12, one at a time, into the vial. Simultaneously, both of the automated dispensing cells 14 may be dispensing twenty solid objects 12, one at a time, into their respective holding tanks 36.

In this manner, by the time the non-automated dispensing cell has filled a first vial, the automated dispensing cells have dispensed their respective twenty solid objects into their holding tanks 36. So instead of returning the first vial, gripping a second vial, and then having to wait for the solid objects 12 to be dispensed one at a time into the second vial, the second vial may be filled by simply opening the gate mechanism 46, allowing the solid objects 12 to drop all at once. Then the second vial may be returned to the user, a third vial may be gripped, the manipulating arm 22 may travel to the next automated cell, and its gate mechanism may open, thereby dispensing the solid objects 12 into the third vial, which is subsequently returned to the user.

So, advantageously, having a combination of the automated dispensing cells 14 and the non-automated dispensing cells 16 in the cabinet 20 of the system 10 increases the efficiency of the system 10. For example, the solid objects 12 of one or more of the automated dispensing cells 14 may be individually dispensed into its holding tank 36 at the same time that the manipulator arm 22 is actuating one of the non-automated dispensing cells 16 to fill one of the empty vials 18 one object at a time. Conversely, in cabinets containing only the non-automated dispensing cells 16, multiple cells 16 can not be actuated at the same time without the addition of more manipulator arms, which is costly and more complex.

However, note that extra space is required for the holding tank 36 and actuators of the automated cells 14, as opposed to the non-automated cells 16, which primarily contain structural and mechanical parts. Therefore, by having a combination of these two types of dispensing cells 14,16, throughput of the system 10 may be increased without greatly decreasing the amount of space available in the cabinet 20 for storing solid objects 12. This allows for a greater variety and quantity of solid objects 12 than would a cabinet entirely comprised of the automated dispensing cells 14.

Although the present technology has been described with reference to the preferred embodiments illustrated in the attached drawings, it is noted that equivalents may be employed and substitutions made herein without departing from the scope of the subject matter recited in the claims.

The invention claimed is:

1. A dispensing cell for dispensing a plurality of solid objects into containers of various dimensions, the dispensing device comprising:
   a first storage bin having an outlet and containing the plurality of solid objects;
   a holding tank having a top opening, a bottom opening, and adjustable sidewalls, wherein the cross sectional area at the top opening of the holding tank is substantially equal to the cross sectional area at the bottom opening, with the cross sectional area at all points between the top opening and the bottom opening being substantially equal,
   a first actuator for actuating the side walls of the holding tank to uniformly expand or contract the cross-sectional area inward of the sidewalls; and
   a gate mechanism which has a first position for blocking the bottom opening of the holding tank to retain the solid objects in the holding tank, and a second position for allowing the solid objects of the holding tank to drop,
   wherein the first storage bin dispenses at least a portion of the plurality of objects through the outlet into the holding tank,
   wherein the holding tank further comprises at least one spring for biasing at least a portion of the sidewalls at a maximum expansion position, such that the holding tank may hold a maximum amount of the plurality of solid objects.

2. The dispensing cell of claim 1, wherein the first actuator applies a force to the sidewalls opposing the force of the at least one spring to decrease the cross-sectional area of the holding tank.

3. The dispensing cell of claim 1, further comprising a second actuator for pivoting the holding tank and the gate mechanism away from the first storage bin to a position for dropping the plurality of objects from the holding tank into one of the containers.

4. The dispensing cell of claim 1, wherein the holding tank walls are actuated by the first actuator when the gate mechanism moves to the second position to dislodge any solid objects remaining in the holding tank.

5. The dispensing cell of claim 1, further comprising a solid object counter disposed between the outlet of the first storage bin and the holding tank to monitor how many solid objects pass from the first storage bin to the holding tank.

6. The dispensing cell of claim 1, wherein the first storage bin is operable to singulate the solid objects and dispense the solid objects into the holding tank one at a time.

* * * * *